United States Patent [19]
Miller

[11] Patent Number: 6,095,505
[45] Date of Patent: Aug. 1, 2000

[54] PATIENT-END HUMIDIFIER

[75] Inventor: Kenneth G. Miller, Santa Ana, Calif.

[73] Assignee: Pegasus Research Corporation, Santa Ana, Calif.

[21] Appl. No.: 09/115,853

[22] Filed: Jul. 15, 1998

[51] Int. Cl.[7] ..................................................... B01F 3/04
[52] U.S. Cl. ........................ 261/130; 261/104; 261/131; 261/137; 261/154; 128/203.27; 128/204.13
[58] Field of Search ............................. 261/99, 104, 130, 261/131, 137, 154, 156; 128/203.17, 203.27, 204.13

[56] References Cited

U.S. PATENT DOCUMENTS

| | | | |
|---|---|---|---|
| 4,038,980 | 8/1977 | Fodor | 128/193 |
| 4,225,542 | 9/1980 | Wall et al. | 261/131 |
| 4,618,462 | 10/1986 | Fisher | 261/131 |
| 4,621,632 | 11/1986 | Bartels et al. | 128/203.27 |
| 4,652,408 | 3/1987 | Montgomery | 261/130 |
| 4,708,831 | 11/1987 | Elsworth et al. | 261/130 |
| 4,911,157 | 3/1990 | Miller | 128/200.21 |
| 4,926,856 | 5/1990 | Cambio, Jr. et al. | 128/203.26 |
| 5,349,946 | 9/1994 | McComb | 128/203.27 |
| 5,558,084 | 9/1996 | Daniell et al. | 128/203.17 |
| 5,588,423 | 12/1996 | Smith | 128/203.26 |

*Primary Examiner*—C. Scott Bushey
*Attorney, Agent, or Firm*—Olson & Hierl, Ltd.

[57] ABSTRACT

An improved breathing gas humidifier including an evaporation module which has a contact chamber and a flash-resistant heat exchanger, a wicking layer on the heat exchanger, a liquid water flow controller, an electric resistance heater, and a breathing gas temperature controller. The contact chamber is defined by a rigid housing and in part by a flash-resistant heat exchanger. The rigid housing has a gas inlet for connection to a breathing gas source such as a ventilator, a water inlet for connection to a liquid water source by a liquid water flow passageway, and a breathing gas outlet connected to an inhalation passageway. The wicking layer is positioned in the contact chamber to receive and distribute liquid water. The breathing gas temperature controller is operably connected to the flow controller, the heater, and a temperature sensor in the breathing gas outlet.

11 Claims, 2 Drawing Sheets

PATIENT-END HUMIDIFIER

TECHNICAL FIELD OF THE INVENTION

This invention relates to inhalation therapy devices and, more particularly, to a humidifier system for producing a humidified and heated breathing gas.

BACKGROUND OF THE INVENTION

Humidifiers are an important part of ventilator breathing circuits because breathing gas must be warm and humidified for optimal inhalation therapy. Humidification is particularly important for patients treated with ventilators for prolonged periods.

Available respiratory humidifiers can generally be placed in one of three groups according to their method of operation: nebulizing, bubbling and heated evaporation. Nebulizing humidifiers rely on the flow of pressurized breathing gas through an ejector-like element to generate an aerosol spray. With bubbling humidifiers, breathing gas is forced directly through a pool of liquid water. Heated-evaporation humidifiers employ a heated contact chamber, where breathing gas is passed over heated water to absorb water vapor.

A persistent, serious problem with all known humidifiers is condensation or "rainout" in the ventilator circuit downstream of the humidifier. As humidified breathing gas travels through tubing towards the patient, it is cooled by ambient air. If the breathing gas is overhumidified or if the room temperature drops, rainout occurs. Therefore, tubing cleanup and system readjustments become all too frequent steps in the maintenance of ventilator circuits.

As discussed in U.S. Pat. No. 5,558,084 to Daniell et al., the rainout phenomena is especially problematic in the home care environment, where precise control of room temperature may be unavailable.

Furthermore, condensation is considered contaminated waste and presents a disposal problem.

Efforts at overcoming the rainout problem are reflected in humidifiers with secondary heaters disposed downstream of the humidifier. For example, U.S. Pat. No. 4,621,632 to Bartels et al. is directed to a humidifier system that includes a coil of resistive heating wires within the breathing hose downstream of a main humidifier device. While those skilled in the art have long recognized that this multi-heater approach is overly complex and therefore expensive, a simpler yet successful approach to solving the rainout problem was previously unavailable.

Heated evaporation humidifiers are thought to suffer somewhat less from the rainout problem because rather than entrained droplets, they generate steam with molecular level distribution. Conventional heatedevaporation humidifiers present the related problem of overheating, however. Without careful monitoring, the temperature of heated water may rise above acceptable limits and cause breathing gas to become dangerously overheated. Equally dangerous are the steam surges produced when liquid water first contacts a dry heater bed following a disruption in water supply.

Another recognized disadvantage of heated evaporation humidifiers is over-dampening of ventilator pressure waves. For artificial respiration, the large gas volumes required in conventional humidifiers over dampen the pressure waves generated by the ventilator to inflate the patient's lungs.

The present invention addresses these and other problems with known humidifiers by providing a breathing gas humidifier with a relatively small gas volume and a flash-resistant evaporation module that can be placed relatively near the patient.

SUMMARY OF THE INVENTION

A breathing gas humidifier of the present invention minimizes operational problems and provides efficient and cost effective control of the moisture content in a breathing gas. The humidifier includes an evaporation module having a contact chamber that is defined by a rigid housing and in part by a flash-resistant heat exchanger. The rigid housing has a gas inlet for connection to a breathing gas source such as a ventilator, a water inlet for connection to a liquid water source through a liquid water flow passageway, and a breathing gas outlet that is connected to an inhalation passageway. A liquid water flow controller in the water flow passageway regulates the flow of liquid water to the contact chamber.

The humidifier further includes a wicking layer positioned in the contact chamber to receive liquid water and an electric resistance heater for heating the heat exchanger. A breathing gas temperature controller is operably connected to the liquid water flow controller, the heater, and a temperature sensor positioned in the inhalation passageway. The breathing gas temperature controller is provided to adjust both the rate of liquid water flow to the evaporation module and the power output of the heater in response to temperature changes in the inhalation passageway.

In a preferred embodiment, the liquid water flow controller is a fixed displacement, metering pump operably associated with a time-proportioning pump controller.

DESCRIPTION OF THE PREFERRED EMBODIMENT

While this invention is susceptible to embodiment in many different forms, this specification and the accompanying drawings disclose only preferred forms as examples of the invention. The invention is not intended to be limited to the embodiments so described, however. The scope of the invention is identified in the appended claims.

A humidifier embodying the features of the present invention provides efficient, cost-effective temperature and humidity control of breathing gas for inhalation therapy. Notably, humidifiers of the present invention also greatly reduce the likelihood of operational problems such as rainout and breathing gas overheating.

Figure 1:
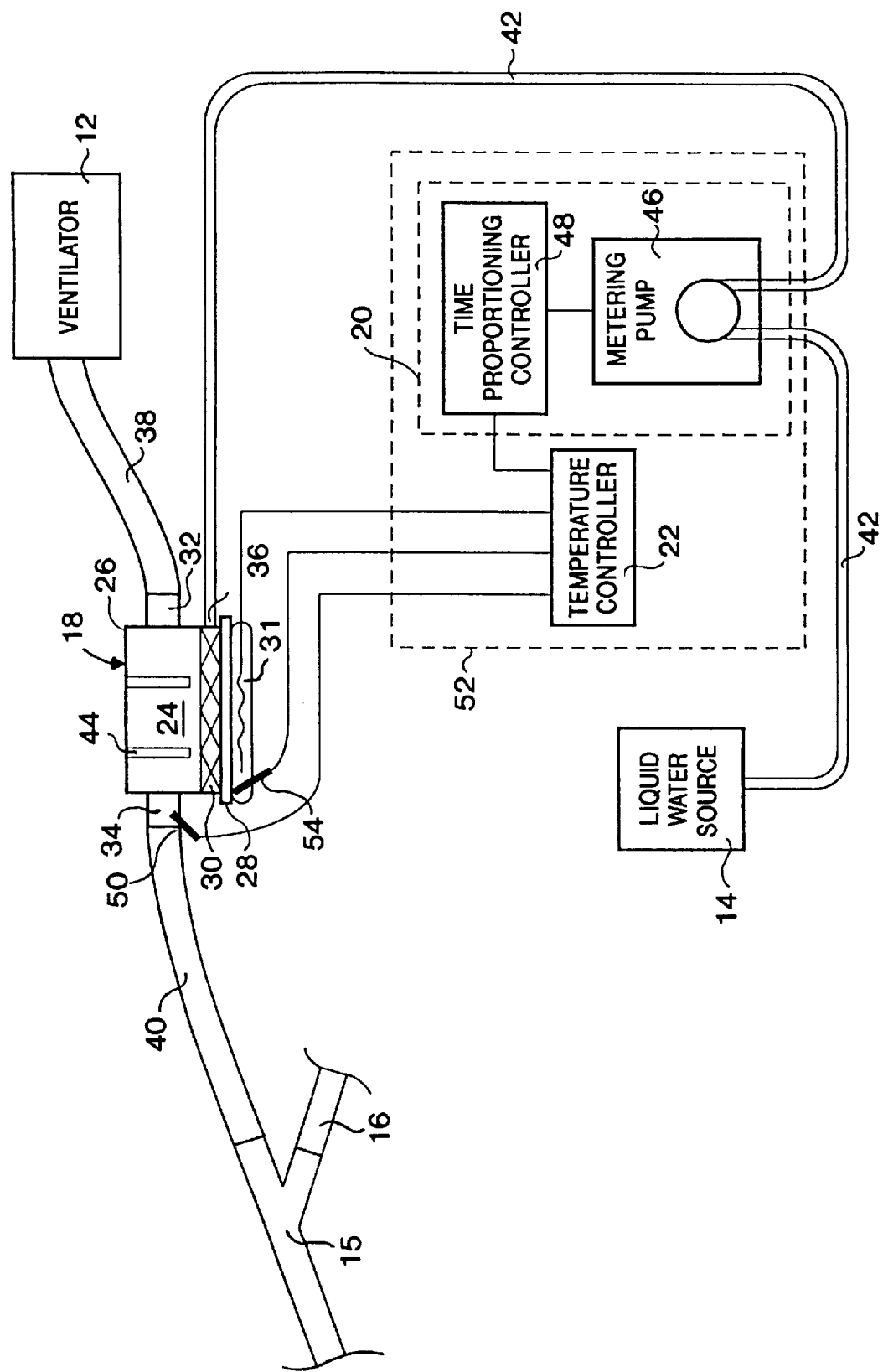
FIG. 1 is a block diagram of a humidifier according to the present invention. Within FIG. 1, a single block may indicate several individual components and/or circuits which collectively perform a single function. Likewise, a single line may represent several individual signal or energy transmission paths for performing a particular operation.

Referring now to FIG. 1, the elements of a humidifier of the present invention are shown connected to a breathing gas source (such as ventilator 12), a liquid water source 14, a patient's "Y" connector 15, and an exhalation passageway 16. Patient's "Y" connector 15 provides a passageway to the mouth or airway of the patient using a suitable mask (not shown) or other adapter.

The humidifier comprises an evaporation module 18, a flow controller 20, and a temperature controller 22. Evaporation module 18 includes a contact chamber 24 defined by a rigid housing 26 and in part by a flash-resistant heat exchanger 28. A wicking layer 30 is positioned in contact with heat exchanger 28, and serves to receive and distribute liquid water entering contact chamber 24. An electric resistive heater 31 is provided for heat exchanger 28 so as to evaporate liquid water arriving in contract chamber 24 from liquid water source 14.

So that breathing gas may pass through evaporation module 18, rigid housing 26 includes a gas inlet 32 and a breathing gas outlet 34. Gas inlet 32 connects to ventilator 12 via a passageway 38, and breathing gas outlet 34 connects to patient's "Y" connector 15, via an inhalation passageway 40. Rigid housing 26 also includes a water inlet 36 for receiving water from water source 14 through a liquid water flow passageway 42.

To better distribute the flow of breathing gas within contact chamber 24, contact chamber 24 may also include gas flow barriers such as baffles 44, which are secured to a wall portion defining the upper part of the chamber 24. Baffles 44 can be perforated, if desired.

Positioned in liquid flow passageway 42 is flow controller 20. Flow controller 20 is preferably a fixed displacement, metering pump 46 operably associated with a time-proportioning pump controller 48. Various types of fixed displacement metering pumps are appropriate for use in the present invention, including peristaltic pumps, diaphragm pumps, piston pumps, bellows-style pumps, and the like. A preferred embodiment of the present invention employs a peristaltic tubing pump.

Metering pump 46 has a fixed, precise delivery rate. By incorporating a timer function, time proportioning controller 48 serves to turn metering pump 46 on for a fixed time period, and thereby control the amount of liquid water delivered to evaporation module 18. Controller 48 accepts a time proportion setpoint, which represents the fraction of a given time period (e.g. about 1 hour) that the pump is turned on.

In addition to providing accurate flow control, metering pump 46 also serves to substantially isolate water source 14 from the breathing gas circuit. With water source 14 isolated, the total volume of space within the breathing circuit, and therefore the related pressure dampening effects, are substantially reduced as compared to conventional humidifiers.

Although FIG. 1 illustrates a humidifier with a flow controller which is a metering-pump and timer combination, other devices that can reliably control the flow of liquid water to evaporation module 18 are also acceptable. For example, a flow meter with control valve type controller can be used to regulate the flow of liquid water from a pressurized source. For this control-valve arrangement, the supply of liquid water may be pressurized by connection to a central supply or by other conventional methods such as an upstream pump or gravity feed achieved by elevating water source 14 above evaporation module 18.

Flow controller 20 is part of the control cascade that includes breathing gas temperature controller 22. Temperature controller 22 can also be characterized as a system control module. Temperature controller 22 is operably connected to flow controller 20, heater 31, and a temperature sensor 50, which is positioned in inhalation passageway 40. Given a user selectable setpoint for breathing gas temperature, controller 22 adjusts both the power to heater 31 and the setpoint of flow controller 20 in response to changes in breathing gas temperature at sensor 50.

As denoted in FIG. 1 by a dashed-line box 52, the controller elements of the present invention are preferably combined into a convenient single module. In this arrangement, the circuitry elements of time proportioning controller 48 and temperature controller 22 may share a power source as well as other required components.

As shown in FIG. 1, temperature controller 22 is optionally configured to accept a signal from a temperature sensor 54 in heater 31. Temperature controller 22 uses the temperature of heater 31 as a safety constraint that limits heating power when the heater temperature exceeds a set high limit. Should the flow of liquid water be inadvertently interrupted, this constraint control feature reduces the risk that evaporation module 18 will generate a surge of steam when the water supply is reestablished.

Figure 2:
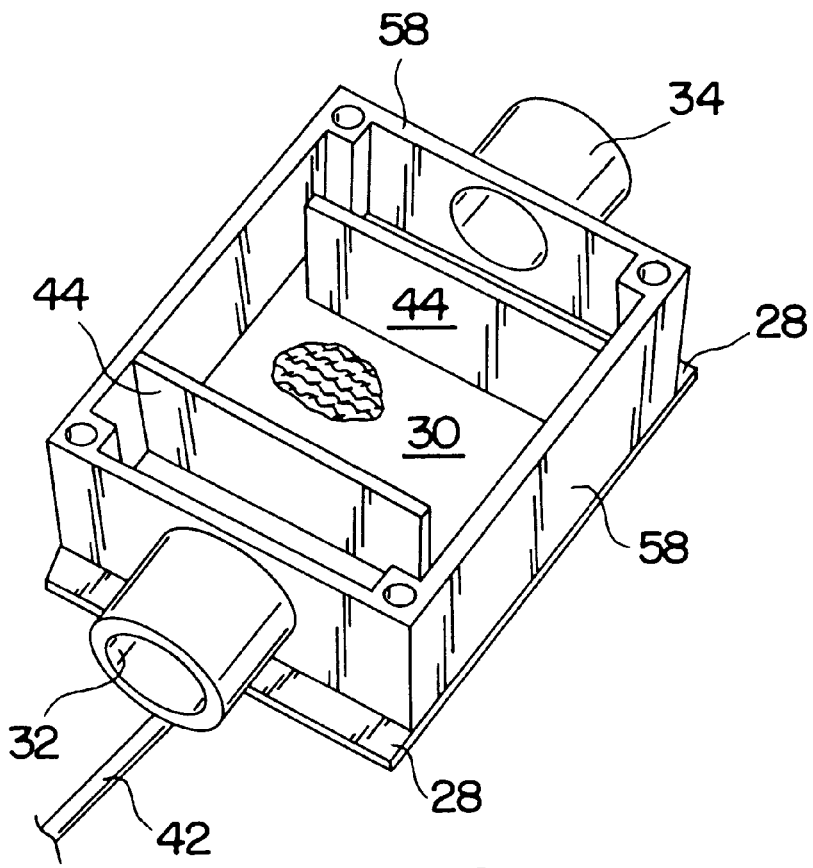
FIG. 2 is a perspective view of an evaporation module according to the present invention shown with its top removed to reveal internal detail.
Figure 3:
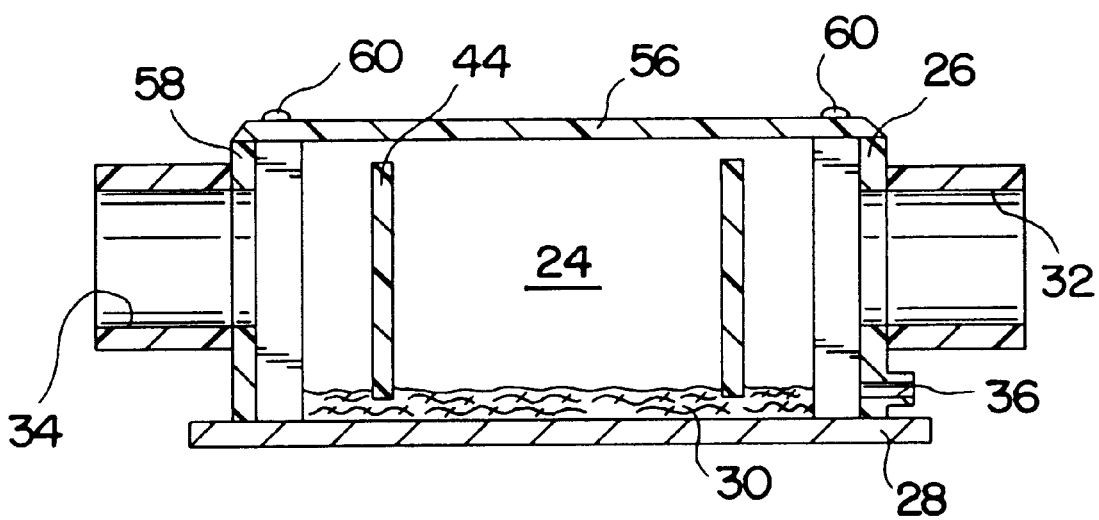
FIG. 3 is a cross sectional view of an evaporation module according to the present invention.

Elements of evaporation module 18, which are represented symbolically in FIG. 1, are shown with more detail in FIGS. 2 and 3. FIG. 2 is a perspective view of evaporation module 18 shown with the top portion removed to reveal internal detail. The cross-sectional view of FIG. 3 shows that rigid housing 26 may include separate cover and side sections as denoted by 56 and 58, respectively. Cover 56 and heat exchanger 28 are secured to side section 58 by a set of fasteners 60, which are preferably bolts or screws.

Evaporation module 18 and its contact chamber 24 are preferably small. In one embodiment of the present invention, the dimensions of contact chamber 24 are 7.6 by 5 by 2.5 centimeters. Defined in terms of volume, contact chamber 24 preferably does not exceed 0.5 liters, and more preferably 0.25 liters.

The bottom, or base, of contact chamber 24 is defined by flash-resistant heat exchanger 28, which is preferably a flat conductive metal plate. Heat exchanger 28 is flash-resistant because it has a relatively low overall heat capacity as compared to the energy required to vaporize liquid water. In a preferred embodiment of the present invention, the heat capacity of the heat exchanger is characterized in that the energy required to raise the temperature of the heat exchanger from 100° C. to 150° C. is less than the energy required to vaporize 1 milliliter of liquid water starting at a temperature of 25° C. and 1 atmosphere pressure.

In accordance with this heat capacity requirement, heat exchanger 28 is relatively thin and of limited mass, thus having a relatively low heat capacity. Specifically, the thickness of heat exchanger 28 is preferably in the range from about 0.03 to about 0.1 centimeters and particularly in the range of about 0.05 centimeters to about 0.08 centimeters. Also in accordance with this heat capacity requirement, heat exchanger 28 is made of a material that is heat conductive yet low in heat capacity. Preferred heat exchanger materials include metals such as aluminum, magnesium, copper, and their alloys. For cost-effectiveness, aluminum or an aluminum alloy is presently a more preferred heat exchanger material of construction.

To enhance its flash-resistance character, the present heat exchangers may include a conductive layer in communication with the contact chamber and an insulating layer between the heater and the conductive layer. By slowing the heat transfer response from heater to heat exchanger, the insulating layer serves to decouple the heat capacity of the heat exchanger from the heat capacity of the heater.

A wide variety of conventional materials are suitable for making rigid housing 26. These include rigid plastics such as acrylic polymers. To aid nursing staff and other ventilator operators in monitoring humidifier operation, rigid housing 26 is preferably made from a transparent plastic material such as a polyacrylate. Inhalation passageway 40, liquid water passageway 42, and the other passageways identified herein, are generally provided by flexible plastic tubing. The present invention is not limited by the selection of conduit materials, however.

Wicking layer 30 is made of an absorptive material, preferably a cotton pad. Other materials, synthetic as well as natural, that facilitate the distribution of liquid water over a surface are also appropriate. The wicking layer need not be made of just one material.

In operation, breathing gas from ventilator 12 passes through passageway 38 and then contact chamber 26, where it absorbs evaporating water before entering patient inhalation passageway 40. The power level for heater 31 and the rate of liquid water flow to evaporation module 18 are set by breathing gas temperature controller 22.

When the temperature of the breathing gas drops, as measured by sensor 50, breathing gas temperature controller 22 responds by increasing both the heating power for evaporation module 18 and the flow rate setpoint for time-proportioning controller 48. In a cascade fashion, time-proportioning controller 48 increases the amount of time metering pump 46 is turned on in a given period.

Humidifiers according to the present invention are preferably designed according to the operating requirements for inhalation therapy applications. These requirements include operating targets for breathing gas in the ranges of 30° C. to 37° C. and 65 to 95 percent relative humidity. In addition, the required breathing gas flow rates vary according to the patient in the range of about 1 liter per minute for infants up to about 30 liters per minute for some adults.

With these factors accounted for, the components of humidifiers according to the present invention are selected or configured for related operating limits. For example, metering pump 46 preferably has a maximum flow capacity of about 50 milliliters per hour. If a higher capacity pump is used, a flow rate limit is preferably set using the pump circuitry or the time-proportioning controller. To reduce the risk of overheating, heater 31 preferably has a maximum power output of about 80 Watts. Also to reduce the risk of overheating, the constraint limit maintained by breathing gas temperature controller 22 for the temperature of heater 31 (measured by sensor 54) is preferably set at about 120–145° C.

Humidifiers of the present invention have several key features including flash-resistance, rainout resistance, and a relatively small gas volume. The flash-resistant feature makes the humidifier suitable for placement near the patient. In a preferred embodiment, the evaporation module is separated from the patient by at most about 70 centimeters of breathing tube. With a close connection to the patient, the risk of rainout in the tubing between evaporation module and patient is substantially reduced.

Humidifiers of the present invention also have a relatively small total gas volume. This low-volume characteristic prevents excessive dampening of ventilator pressure waves, making breathing circuit pressure profiles easier to control.

Numerous variations and modifications of the embodiments described above may be effected without departing from the spirit and scope of the novel features of the invention. It is to be understood that no limitations with respect to the specific system illustrated herein are intended or should be inferred. It is, of course, intended to cover by the appended claims all such modifications as fall within the scope of the claims.

I claim:

1. A humidifier for a breathing gas comprising:

an evaporation module including a contact chamber defined by a rigid housing and in part by a flash-resistant heat exchanger, said rigid housing having a gas inlet connectable to a breathing gas source, a water inlet connectable to a liquid water source by a liquid water flow passageway, and a breathing gas outlet connected to an inhalation passageway;

a temperature sensor in said breathing gas outlet;

a wicking layer in the contact chamber, in contact with said heat exchanger and positioned to receive liquid water entering said contact chamber;

an electric resistance heater for said heat exchanger;

a liquid water flow controller in said water flow passageway; and a breathing gas temperature controller operably connected to said flow controller, said heater, and said sensor for adjusting the water flow rate to said evaporation module and the power to said heater in response to temperature changes in said breathing gas outlet.

2. The humidifier according to claim 1 wherein said flow controller is a fixed displacement, metering pump operably associated with a time-proportioning pump controller.

3. The humidifier according to claim 2 wherein said metering pump is selected from the group consisting of a peristaltic pump, a diaphragm pump, a piston pump, and a bellows pump.

4. The humidifier according to claim 1 wherein said water flow controller and said breathing gas temperature controller are combined in a single module.

5. The humidifier according to claim 1 wherein the energy required to raise the temperature of said heat exchanger from 100° C. to 150° C. is less than the energy required to vaporize 1 milliliter of liquid water starting at a temperature of 25° C. and 1 atmosphere pressure.

6. The humidifier according to claim 1 wherein said heat exchanger is a substantially flat metal plate defining the base of said contact chamber.

7. The humidifier according to claim 6 wherein said heat exchanger includes a thermally conductive layer exposed in said contact chamber and a thermal insulation layer between said conductive layer and said heater.

8. The humidifier according to claim 6 wherein said metal plate has a thickness in the range of about 0.05 centimeters to about 0.08 centimeters.

9. The humidifier according to claim 1 wherein said heat exchanger comprises a metal selected from the group consisting of aluminum, magnesium, and copper, and alloys thereof.

10. The humidifier according to claim 1 wherein the volume of said contact chamber is at most 0.5 liters.

11. The humidifier according to claim 1 wherein the wicking layer is cotton.

* * * * *